United States Patent [19]

Bachman et al.

[11] Patent Number: 5,235,075

[45] Date of Patent: Aug. 10, 1993

[54] PURIFICATION OF PROPYLENE OXIDE

[75] Inventors: Gene W. Bachman; Robert K. Brown, both of Baton Rouge, La.

[73] Assignee: The Dow Chemical Company, Midland, Mich.

[21] Appl. No.: 988,568

[22] Filed: Dec. 10, 1992

[51] Int. Cl.$^5$ .................. C07D 301/32; C07D 303/04
[52] U.S. Cl. .................................... 549/542; 521/189; 568/679
[58] Field of Search ........................................ 549/542

[56] References Cited

U.S. PATENT DOCUMENTS 4,233,202 11/1980 Berger et al. ........................ 549/542
4,692,535 9/1987 Larson et al. ........................ 547/542

OTHER PUBLICATIONS

"Diatomite", Kirk-Othmer Encyclopedia of Chemical Technology, vol. 7, pp. 603-614, 3rd ed., 1979.

Primary Examiner—Joseph E. Evans

[57] ABSTRACT

A process for purifying propylene oxide containing an unacceptable quantity of poly(propylene oxide) contaminant having a molecular weight of at least about 50,000, which comprises contacting the so-contaminated propylene oxide with a quantity of a substantially non-calcined diatomaceous earth for a time and under conditions sufficient to reduce the amount of such contaminant in such propylene oxide to acceptable levels, and recovering the purified propylene oxide product. Also, processes for making polyether polyols from such purified propylene oxide products, and for making high resilient flexible polyurethane foams from such polyols.

14 Claims, No Drawings

PURIFICATION OF PROPYLENE OXIDE

The present invention relates to processes for the purification and/or separation of propylene oxide. The present invention relates more particularly to a process of the type described in U.S. Pat. No. 4,692,535 to Larson et al. (hereafter, Larson), wherein a propylene oxide product suitable as an intermediate in the production of polyether polyols for high resilient flexible polyurethane foam applications is made by removing substantially all of a high molecular weight poly(propylene oxide) fraction from an otherwise commercially-acceptable propylene oxide.

As disclosed in the Larson patent, propylene oxide of an otherwise commercially-acceptable purity was found to contain a certain nonvolatile impurity (namely, poly(propylene oxide) (or PPO) having a molecular weight of at least 50,000), which impurity made the propylene oxide unsuitable for making polyether polyols to be used with a polyisocyanate and blowing agent in the manufacture of acceptable high resilient flexible polyurethane foams. Polyether polyols prepared from propylene oxide having in excess of 0.1 parts per million by weight of the high molecular weight poly(propylene oxide) impurity were determined to lead to low foam rise and substantial blow hole formation in the polyurethane foams, whereas polyether polyols made from propylene oxide having reduced levels of the high molecular weight PPO impurity produced polyurethane foams with good foam rise and without substantial blow hole formation.

The solution proposed by Larson involved filtering or percolating either crude liquid propylene oxide of 95 percent or greater propylene oxide content or propylene oxide of otherwise commercially-acceptable, 99 percent purity or better through a fixed bed of an adsorbent material. The adsorbent materials suggested by Larson as suitable for this purpose are activated carbon, charcoal and attapulgite, and granular forms are said to be preferable to powdered forms of these materials. The quantities of adsorbent to be used per unit volume of propylene oxide to be treated are estimated at from about 0.001 to about 0.01 grams or more of solid adsorbent per gram of propylene oxide, with contact times ranging from about 1 to about 15 minutes, temperatures of from about 10 to about 100 degrees Celsius and pressures ranging from atmospheric to superatmospheric.

SUMMARY OF THE PRESENT INVENTION

The present invention provides, as in Larson, a process for purifying propylene oxide containing an unacceptable quantity of a poly(propylene oxide) polymer contaminant having a molecular weight of at least about 50,000, wherein the process comprises contacting the propylene oxide with a substantially non-calcined diatomaceous earth for a time and under conditions sufficient to reduce the amount of said contaminant to acceptable levels, and thereafter recovering the purified propylene oxide product. "Unacceptable" and "acceptable" in this context refer to those levels of the poly(propylene oxide) contaminant which make the polyether polyols produced from propylene oxide containing such levels of such contaminant commercially unacceptable or acceptable, respectively, for making high resilient flexible polyurethane foams.

In another, related aspect, the invention provides a process for making polyether polyols from propylene oxide, wherein the propylene oxide has been purified according to the process described in the preceding paragraph. In still another aspect, a process for making high resilient flexible polyurethane foams from the just-mentioned polyether polyols is provided.

DETAILED DESCRIPTION OF THE PREFERRED EMBODIMENTS

As summarized in Kirk-Othmer Encyclopedia of Chemical Technology, 3rd ed., Vol. 7 at pages 603–614 (1979), diatomaceous earth (sometimes also referred to as kieselguhr or diatomite) is a sedimentary rock of marine or lacustrine deposition, and consists mainly of accumulated shells or frustules of hydrous silica secreted by diatoms (microscopic, one-celled, flowerless plants of the class Bacillarieae).

Diatomaceous earth consists in chemical terms primarily of silicon dioxide, albeit in a different physical structure than typically encountered. Impurities typically include other aquatic fossils, sand clay, volcanic ash, calcium carbonate, magnesium carbonate, soluble salts and organic matter, while a typical spectrographic analysis on a dry basis may show $SiO_2$, $CaO$, $MgO$, $Al_2O_3$, $Fe_2O_3$, $Na_2O$, $V_2O_5$, and $TiO_2$. The chemically combined water content can vary from 2 to 10 percent by weight.

In physical terms, most diatomaceous earths are powders, having mean particle diameters ranging from 20 to 0.75 micrometers, although aggregates can be obtained having 1.27 centimeter diameters down to fine powders.

Some diatomaceous earths are suitable for use in the process of the present invention, while others are not well-suited for this use. Given the variety of grades of diatomaceous earth which are available, it has not been possible to test every grade and to precisely segregate those which will prove adequate from those which will not. As a rule, though, suitable diatomaceous earths are those which are substantially non-calcined. Minimally calcined materials, which do not display the dramatic reductions in BET surface area and in the small volume pores characteristic of calcination and flux-calcination, are expected to have some degree of activity in the present process.

Preferred diatomaceous earths will not have been pyrolyzed to any appreciable extent, however, at the 500 to 550 degree Fahrenheit temperatures typically employed for such pyrolysis, and freshwater-origin (lacustrine) diatomaceous earths as a class to work better than marine-origin diatomaceous earths.

Also, it would appear that those diatomaceous earths characterized as having a high surface area (e.g., a BET surface area of at least about 15 square meters per gram, more preferably about 35 square meters per gram and most preferably about 60 square meters per gram), a typical Type IV isotherm plot (as measured by conventional gas adsorption techniques) manifesting a degree of hysteresis which corresponds to differences in the adsorption and desorption surface areas of a particular diatomaceous earth of at least 15 percent, preferably at least 40 percent and most preferably at least 80 percent, and a substantial proportion of pores with a radius of from about 20 Angstroms to about 100 Angstroms (i.e., having an average pore radius of less than about 120 Angstroms) should work well in the proposed process.

A most preferred, freshwater-origin diatomaceous earth is sold commercially as "ODW" grade diatomaceous earth (Oil-Dri Corporation of America). This particular diatomaceous earth is mined in Oregon from two sites, and thus a claim "A" material is available as well as a claim "C" material. The claim "C" material, from Christmas Valley, Oreg., is preferred. The claim "C" material has a reported resistance to attrition, as measured by ASTM test method E-728, of 73.9 percent and is well-suited for use in a column treatment process of the present invention (described below). The ODW-C grade diatomaceous earth is not considered by its supplier to have been pyrolyzed appreciably, and unlike most of the commercially-available diatomaceous earths has been crushed but not hammer-milled.

The claim "C" earth is further characterized by a high BET surface area of about 63 square meters per gram, by an average pore radius of about 107 Angstroms, and adsorption and desorption surface areas of about 57.5 and 108.5 square meters per gram of adsorbent, respectively, whereby such areas differ by about 88 percent. Significant hysteresis is exhibited by the claim "C" material from a relative pressure $P/P_O$ of 0.45 up to relative pressures of 0.95 and greater. Substantially less than 1 percent of the pores in the ODW-C material are classifiable as micropores, i.e., as having a pore radius of 10 Angstroms or less.

The process of the present invention is readily adaptable to commercial industrial operations, and involves as indicated above the removal of high molecular weight poly(propylene oxide) (having a molecular weight generally of at least 50,000, for example) from crude propylene oxide of 95 percent or greater propylene oxide content or from propylene oxide of an otherwise commercially-acceptable purity.

The purified propylene oxide, containing preferably less than about 100 parts per billion by weight of the high molecular weight poly(propylene oxide) as determined by an analytical procedure described more particularly below, more preferably less than about 65 parts per billion and most preferably less than about 50 parts per billion of such contaminant, is suitable for direct conversion (generally with one or more other organic oxides) to highly pure polyether polyols via reaction (normally catalyzed) with an initiator containing two or more active hydrogens. These polyols then react with an isocyanate in the presence generally of water and other conventional materials, e.g., inorganic fillers, surfactants, catalysts, auxiliary blowing agents, and provide flexible, stable polyurethane resilient foams exhibiting high rise while being substantially free of blowhole formation. The processes of producing polyether polyols from oxides including propylene oxide and of producing high resilient flexible polyurethane foams from such polyols are well-known in the art and are broadly summarized and described in "Flexible Polyurethane Foams", Herrington and Hock (Dow Plastics, 1991), so that no additional explanation or description need be offered herein.

The propylene oxide starting material of the purification process of the present invention may be obtained by any of the known routes for the production of propylene oxide. The purification process of the present invention is most conveniently effected at any time after propylene oxide of an otherwise suitable commercial purity has been obtained and the poly(propylene oxide) contaminant formed therein at unacceptable levels.

Preferably the inventive purification process is followed by prompt conversion of the purified propylene oxide product into the desired polyether polyols, or by shipment or storage of the purified product in a vessel which is made of a conventional carbon steel but which is kept at a low temperature (e.g., about 7 degrees Celsius) or in a vessel constructed of or lined with a suitable material (e.g., a stainless steel such as is preferably used for constructing treatment vessels for performing the present process). In this regard, conventional carbon steels were found by Larson to catalyze over a period of time at a given temperature the formation of the undesired high molecular weight poly(propylene oxide) contaminant.

Whereas in Larson it is important that the propylene oxide be contacted with a bed of solid adsorbent rather than being slurried therewith and separated therefrom by filtration, in the present invention it should be appropriate to either use a bed of diatomaceous earth with filtration or to form a slurry and filter the treated material.

In a first embodiment of the process, then, propylene oxide liquid is passed through a bed of diatomaceous earth, e.g., by a conventional static-bed percolation process wherein the propylene oxide to be refined is passed through a stationary bed of the diatomaceous earth under controlled conditions. This purification process is continued until the product propylene oxide has attained the desired poly(propylene oxide) contaminant content. The treatment with the diatomaceous earth may generally be conducted at temperatures in the range of from about 0 degrees Celsius to about 35 degrees Celsius, and at atmospheric or superatmospheric pressures, e.g., up to about 100 psig.

It is considered, based on tests with a 4 in. diameter pilot column, that a presently-preferred apparatus for conducting the process will operate at about 70 psig and about 15 degrees Celsius and will comprise two or more stainless steel columns operating in series, in parallel, or preferably operating in a rotation. Assuming a feed concentration in the propylene oxide to be treated of about 150 parts per billion by weight of the high molecular weight poly(propylene oxide) and a targeted concentration in the purified propylene oxide of about 50 parts per billion, each column will preferably employ the Oil-Dri grade "C" material in a 15 foot long bed contained between plates equipped with Johnson screens, and operate at a flow rate into the bed of 1 gallon per minute per square foot. Stainless steel in-line cartridge filters (3 micron absolute, 1 micron nominal) will be used to catch any fines from the bed of diatomaceous earth.

It is expected that the beds will have an effective lifetime of at least about 3 months before the diatomaceous earth requires replacement or regeneration, with replacement presently appearing to be a much more viable approach than regeneration. A preferred method of replacing the diatomaceous earth will comprise water-washing the diatomaceous earth until the total organic content (TOC) in the effluent is less than about 50 parts per million, then refilling the column with water and heating the water-filled column to 100 degrees Celsius for about 25 hours, for example, to convert any residual propylene oxide to propylene glycol. The column can then be flushed of the water, and the diatomaceous earth removed by vacuum truck and disposed of. Given the time involved in removing the diatomaceous earth by this process, it is again generally to be preferred for columns to be operated in a rotation rather than in series or parallel so that not all columns need to be taken off-line at any given time.

Those skilled in the art will appreciate however that the optimum parameters of operation for any given stationary bed arrangement will depend on, for example, the diatomaceous earth employed and on the degree of purification required, but it is considered that these persons will be well able to select those parameters given the present disclosure.

In the second, less-preferred embodiment of the purification process of the present invention, liquid propylene oxide to be treated is slurried directly with the diatomaceous earth, and thereafter filtered to remove the diatomaceous earth from the purified liquid propylene oxide product. A Funda Type R pressure leaf filter from Steri Technologies, Inc. is considered as suitable for the primary filtering operation, to be followed preferably by a disposable cartridge-type filter as a finishing filter. Sub-micron (e.g., 0.8 micron) rated filter cartridges of pleated design should be suitable as finishing filters.

Operating pressures for the pressure leaf filter will preferably be in the range of about 30 psig. Assuming again a starting PPO concentration in the liquid propylene oxide feed of about 150 parts per billion by weight, it is expected that a residence time in the primary filter of from about 5 to about 30 minutes, and especially about 10 minutes or less, should be sufficient (with an initial loading of the Oil-Dri ODW grade C diatomaceous earth material in the propylene oxide liquid of about 0.05 percent by weight) to achieve the desired reduction in PPO levels.

Stainless steel mesh with 10-micron nominal pore rating would serve as a suitable filter medium, and the design flow rate for sizing the filter area will preferably be from about 1.0 to 1.5 gallons per minute per square foot. The average porosity of deposited diatomaceous earth filter cakes can be expected to measure about 0.65 to about 0.70, and with the diatomaceous earth solids concentration can be used to provide a check on the filter area and accompanying filter volume available to hold the diatomaceous earth filter cake before discharge and disposal by appropriate means and methods.

ILLUSTRATIVE EXAMPLES

To further illustrate the present invention and the manner in which it may be practiced, the following specific examples are set forth. In the examples, unless otherwise indicated, all parts and percentages are by weight.

EXAMPLE 1

An apparatus was assembled for flowing a volume of commercial-purity liquid propylene oxide (containing poly(propylene oxide) having a molecular weight of at least about 50,000 as a contaminant) through a bed of diatomaceous earth, and comprised a 500 mL dropping funnel mounted atop a water-jacketed chromatographic column (1 inch in diameter by 18 inches long). A glass collection bottle was placed at the bottom of the chromatographic column for collecting purified propylene oxide, and a nitrogen bubble was established for the collection.

The procedure for using this apparatus involved adding about 1 liter of the propylene oxide to be treated to a 2000 mL glass beaker. About 100 grams (or approximately 200 mL) of "ODW" grade, claim "C" diatomaceous earth (granular, from Oil Dri Corporation of America) were added with stirring to the beaker, using a thermometer to watch for any exotherms suggestive of reactivity. This mixture was allowed to come to room temperature.

Meanwhile, the apparatus was assembled, using a glass wool plug in the bottom of the column, a control valve at the bottom of the column, and beginning water cooling (water temperature was about 20 degrees Celsius). Most of the liquid propylene oxide was then decanted off from the beaker, without letting the diatomaceous earth become dry. The beaker was then swirled, and the contents emptied down the side of the column. Once the diatomaceous earth was settled into place at the bottom of the column, the propylene oxide to be treated was placed in the dropping funnel, and a flow started corresponding to a treatment rate of about 2.5 bed volumes (or about 500 mL) per hour. To prevent free-fall of the propylene oxide and the possibility of a static charge being generated, flow of the propylene oxide into the column was matched to the flow out of the column, so that the level of propylene oxide in the column was at least to the bottom of the dropping funnel at all times.

The treated propylene oxide was collected in a bottle under a nitrogen bubble, with the delivery tube from the column extending to the bottom of the collection bottle to minimize fluid free fall and static charges. The propylene oxide collected in this manner was then filtered through Whatman No. 3 filter paper and the filtrate tested for poly(propylene oxide).

The test method employed for analyzing poly(propylene oxide) in this Example, as well as in Examples 2 and 3 below, was designed to provide a quantitative indication for poly(propylene oxide) having a molecular weight of about 40,000 and higher, based on polystyrene standards (polystyrene standard kit, narrow distribution, available from Polymer Laboratories (Cat. No. 2010-0100)). The method's lower limit of detection was about 10 parts per billion by weight.

According to the test method, the non-volatile residue from a sample of propylene oxide (treated or untreated) was dissolved in a small amount of tetrahydrofuran (THF) and chromatographed on a single gel permeation chromatography (GPC) column (Ultrastyragel TM -type (Part No. 10571), 500 angstrom pore size, 300 mm long by 7.8 mm diameter, Waters Associates) under conditions maximizing sensitivity (i.e., 1.2 mL/minute eluent flowrate, 40 degrees Celsius (column and detector), injection volume of 300 $\mu$L). A precolumn filter was used (2 micrometer frit, Part No. 84560 from Waters Associates), and the injection valve was a six port unit with a 300 microliter loop.

The pore size of the column was selected such that all high molecular weight components eluted as a single peak at the column's exclusion limit. A differential refractive index detector (Model 1047 differential refractive index detector from Hewlett-Packard Company) was then used, and quantitation performed by peak height comparison to a polyglycol (polypropylene glycol P-2000 grade, The Dow Chemical Company) standard solution (0.1 grams with THF to 100 mL, then 2 mL taken and further diluted to 100 mL with additional THF.

Propylene oxide samples (150 mL in volume) to be analyzed were transferred from glass sample bottles to a clean, dry evaporating dish, which was then placed on a temperature bath in a fume hood at about 30 to 50 degrees Celsius for about 1 to 2 hours.

The evaporating dish containing any non-volatile residue was then dried in an oven at 105 to 110 degrees Celsius for about 30 minutes, and then cooled in a desiccator for another 30 minutes.

After obtaining a baseline and standardizing with the polyglycol standard, the oven-dried and desiccator-cooled evaporating dish was tared on an analytical balance and 1.5 mL of THF were added with swirling to dissolve any PPO present in the non-volatile residue, using a glass Petri dish as a cover to minimize THF evaporation. The dish was then reweighed to obtain the weight of THF left, and a 1-mL glass syringe was filled with the sample. After flushing the loop of the injection valve with 1 mL of THF, the sample was then injected. The peak height at the exclusion limit of 4.8 minutes was measured, and the concentration of PPO in parts per billion by weight was calculated as follows:

$$PPb\ of\ PPO = (Pk\ Ht, Spl) \times (CSTD) \times (Wt\text{-}THF) \times 1362 \times (Pk\ Ht, Std) \times (Vol\text{-}PO),$$

where
- Pk Ht, Spl is the peak height of the sample at a given attenuation,
- Pk Ht, Std is the peak height of the polyglycol standard at the same attenuation,
- CSTD is the actual concentration of the standard in micrograms per milliliter, calculated by multiplying the actual weight of the P-2000 polyglycol used (to the nearest 0.001 grams) by 200, and
- Vol-PO is the volume of propylene oxide evaporated in mL.

Where the calculated concentration of high molecular weight PPO exceeds 11,000 but is less than 50,000 ppb, the analysis is repeated using 30.0 mL of propylene oxide to start. Where the calculated concentration is between 50,000 and 200,000 ppb, the starting volume of PO is reduced to 3.0 mL, and for levels of between 200,000 and 1,000,000 parts per billion the starting amount of propylene oxide is reduced to 0.3 mL.

Because this method is not specific to high molecular weight PPO, care was taken throughout this and subsequent Examples to prevent sample contamination with other high molecular weight species.

The untreated propylene oxide of this Example, when analyzed by the apparatus and procedure described above, yielded a peak at 4.385 minutes corresponding to a starting PPO level of 471 parts per billion. After treatment, the level of PPO by this method was determined to be just under 10 ppb (9.6 ppb).

EXAMPLE 2

For this example, 0.25 grams of the diatomaceous earth of Example 1 were powdered in a mortar and pestle and sifted through a 60 mesh (U.S. series) sieve. The powdered diatomaceous earth was thereafter used in a slurry-type process with 750 mL of liquid propylene oxide to be treated thereby. After mixing the liquid propylene oxide and powdered diatomaceous earth on a shaker for 2 hours and filtering through a Whatman No. 3 filter, the treated and filtered propylene oxide material was tested for PPO levels as described in Example 1. By this testing the starting high molecular-weight PPO level was determined to be 120 parts per billion, whereas after treatment the PPO level had dropped to about 15 parts per billion.

To ensure that the treatment with diatomaceous earth did not interfere with other properties of commercial interest (e.g., APHA color, ethylene oxide content, weight percent water, total acids, total chlorides, total aldehydes), the treated propylene oxide of this Example was tested for these properties by conventional, commercially-practiced methods and in each property the treated propylene oxide was determined to be of a commercially-acceptable nature.

EXAMPLE 3

For this example, 0.25 grams of the same powdered diatomaceous earth as used in Example 2 were again used in a slurry-type process with 750 mL of liquid propylene oxide to be treated thereby. After mixing the liquid propylene oxide and powdered diatomaceous earth on a shaker for 2 hours and filtering through a Whatman No. 3 filter, the treated and filtered propylene oxide material was tested for PPO levels as in previous examples.

The propylene oxide before treatment contained 398 parts per billion of poly(propylene oxide), whereas after treatment the propylene oxide contained about 30 parts per billion by weight of the high molecular weight poly(propylene oxide).

EXAMPLES 4–6

These examples are concerned with verifying the appropriateness of the treated propylene oxide materials from Examples 1-3 in the manufacture of polyether polyols for high resilient flexible polyurethane foams. In this regard, the object was to confirm that reducing the concentration of the high molecular weight poly(propylene oxide) contaminant to the levels shown in Examples 1-3 and taught in Larson (below 100 ppb) would produce a suitable propylene oxide product, whether by a column treatment or by a slurry-based treatment process.

Polyether polyols were accordingly prepared from the various treated propylene oxide materials of Examples 1-3, by a manufacturer of polyols for high resilient flexible polyurethane foam applications. Polyurethane foam formulations were then prepared from each of these polyols.

The resulting foams were evaluated for blowholes and foam rise. The foam associated with the untreated propylene oxide material in Example 1 (PPO level of 471 ppb) was rated as unacceptable (a "3" on a scale of 0 to 10, with 0-1 being acceptable and 2-10 being unacceptable), while the treated material (PPO level of just under 10 ppb) was rated a "0".

The foam produced from the untreated material of Example 2 (PPO level of 120 ppb) was given a "1", while the treated material was again rated a "0".

The foam produced from the untreated propylene oxide material of Example 3 (PPO level of 398 ppb) was unacceptable at a "3" rating, whereas after treatment the purified propylene oxide product (PPO level of about 30 ppb) was given an optimum, "0" rating.

EXAMPLES 8 AND 9

These examples are directed to the establishment of an adsorption isotherm for the ODW-C diatomaceous earth employed in previous examples, so that the activity of the ODW-C material can be compared to the activities of three other diatomaceous earths (Examples 10-15 below).

In Example 8, four portions of the ODW-C material which had been pulverized and sieved through a 60 mesh screen were weighed and placed in 500 mL glass bottles. A sample of 250 mL of a propylene oxide containing 463 parts per billion of the high molecular weight propylene oxide contaminant was then added to the ODW-C portion in each bottle. The bottles were capped with Teflon ™ sealed caps and placed on a reciprocating shaker. The samples were shaken for 2 hours at 260 oscillations per minute, and then filtered through a Whatman No. 3 filter paper using a Millipore pressure filter apparatus. The propylene oxide was analyzed for PPO by the normal procedure, with the results listed below in Table 1:

TABLE 1

| Wt. ODW-C (g) | Vol. PO | PPB, Start | PPB, Final | C (mg/l) | q (g PPO/g ads.) |
|---|---|---|---|---|---|
| 0.100 | 250 | 463 | 20 | 0.017 | 9.19E-04 |
| 0.050 | 250 | 463 | 21 | 0.017 | 1.83E-03 |
| 0.025 | 250 | 463 | 83 | 0.069 | 3.15E-03 |
| 0.010 | 250 | 463 | 273 | 0.197 | 4.69E-03 |

For Example 9, four new samples were run according to the same procedure. These results are found in Table 2:

TABLE 2

| Wt. ODW-C (g) | Vol. PO | PPB, Start | PPB, Final | C (mg/l) | q (g PPO/g ads.) |
|---|---|---|---|---|---|
| 0.100 | 250 | 457 | 35 | 0.029 | 8.76E-04 |
| 0.050 | 250 | 457 | 13 | 0.011 | 1.84E-03 |
| 0.026 | 250 | 457 | 79 | 0.066 | 3.02E-03 |
| 0.013 | 250 | 457 | 234 | 0.194 | 3.56E-03 |

EXAMPLES 10 AND 11

The procedure of Examples 8 and 9 above was followed for four samples of Dicalite 104 ™ grade diatomaceous earth from Grefco, Inc., Torrance, Calif. The Dicalite ™ material which was used in these Examples is a freshwater origin material mined in Basalt, Nev., and has previously been dried, pulverized and air-classified to remove impurities. The material has a measured BET surface area of 34.49 square meters per gram, an average pore radius of 84 Angstroms, an adsorption surface area of 24.7 sq. meters per gram, and a desorption surface area of 25.1 sq. meters per gram with about 25 percent of its pores being micropores of a radius of 20 Angstroms or less.

The results from the initial four samples are shown in Table 3:

TABLE 3

| Wt. Ads. (g) | Vol. PO | PPB, Start | PPB, Final | C (mg/l) | q (g PPO/g Ads.) |
|---|---|---|---|---|---|
| 0.100 | 250 | 463 | 156 | 0.129 | 6.37E-04 |
| 0.050 | 250 | 463 | 274 | 0.227 | 7.84E-04 |
| 0.025 | 250 | 463 | 371 | 0.308 | 7.64E-04 |
| 0.010 | 250 | 463 | 376 | 0.312 | 1.81E-03 |

Four additional samples provided the results shown in Table 4:

TABLE 4

| Wt. Ads. (g) | Vol. PO | PPB, Start | PPB, Final | C (mg/l) | q (g PPO/g Ads.) |
|---|---|---|---|---|---|
| 0.104 | 250 | 624 | 235.7 | 0.196 | 7.75E-04 |
| 0.053 | 250 | 624 | 461.6 | 0.383 | 6.36E-04 |
| 0.024 | 250 | 624 | 544.1 | 0.452 | 6.91E-04 |
| 0.013 | 250 | 624 | 553.8 | 0.460 | 1.12E-03 |

EXAMPLES 12 AND 13

Four samples of Filter-Cel ™ diatomaceous earth from Celite Corporation, Lompoc, Calif., were weighed and placed in 500 mL glass bottles. Sample weights were taken, and 250 mL of a propylene oxide containing 1050 parts per billion of the high molecular weight poly(propylene oxide) were added to each bottle. The procedure outlined in Examples 8 and 9 was then followed, with the results reported below in Table 5. The Filter-Cel ™ diatomaceous earth material tested herein is a marine diatomite mined in Lompoc, Calif. and has previously been dried, pyrolyzed and air-classified. This material has a measured BET surface area of 17.27 sq. meters per gram, an average pore radius of 95 Angstroms, an adsorption surface area of 13.1 square meters per gram and a desorption surface area of 15.4 square meters per gram, with about 15 percent micropores.

TABLE 5

| Wt. Ads. (g) | Vol. PO | PPB, Start | PPB, Final | C (mg/l) | q (g PPO/g Ads.) |
|---|---|---|---|---|---|
| 0.102 | 250 | 1050 | 681 | 0.565 | 7.51E-04 |
| 0.050 | 250 | 1050 | 814 | 0.676 | 9.79E-04 |
| 0.025 | 250 | 1050 | 946 | 0.785 | 8.63E-04 |
| 0.012 | 250 | 1050 | 1040 | 0.863 | 1.73E-04 |

Four new samples, working on a different propylene oxide, yielded the results shown in Table 6:

TABLE 6

| Wt. Ads. (g) | Vol. PO | PPB, Start | PPB, Final | C (mg/l) | q (g PPO/g Ads.) |
|---|---|---|---|---|---|
| 0.100 | 250 | 420 | 223.7 | 0.186 | 4.07E-04 |
| 0.050 | 250 | 420 | 206.5 | 0.171 | 8.86E-04 |
| 0.027 | 250 | 420 | 317.6 | 0.264 | 7.87E-04 |
| 0.013 | 250 | 420 | 411.5 | 0.342 | 1.40E-04 |

EXAMPLES 14 AND 15

The procedure followed in Examples 8-13 was followed again with four samples of Standard Super-Cel ™ diatomaceous earth from Celite Corporation. This particular material is a marine origin diatomite from Lompoc, Calif., and has previously been calcined at 1800 degrees Fahrenheit to allow higher flowrates during conventional filtering operations. The Standard Super-Cel ™ diatomaceous earth has a measured BET surface area of 2.59 square meters per gram, an average pore radius of 169 Angstroms, an adsorption surface area of 1.63 square meters per gram and a desorption surface area of 2.40 square meters per gram. The results of the testing with these four initial samples is reported in Table 7 as follows:

TABLE 7

| Wt. Ads. (g) | Vol. PO | PPB, Start | PPB, Final | C (mg/l) | q (g PPO/g Ads.) |
|---|---|---|---|---|---|
| 0.101 | 250 | 430 | 407 | 0.338 | 4.73E-05 |
| 0.051 | 250 | 430 | 384 | 0.319 | 1.87E-04 |
| 0.026 | 250 | 430 | 415 | 0.344 | 1.21E-04 |
| 0.013 | 250 | 430 | 434 | 0.360 | −6.59E-05 |

A followup run with four new samples gave the results shown in Table 8:

TABLE 8

| Wt. Ads. (g) | Vol. PO | PPB, Start | PPB, Final | C (mg/l) | q (g PPO/g Ads.) |
|---|---|---|---|---|---|
| 0.106 | 250 | 500 | 407496.6 | 0.412 | 6.64E-06 |
| 0.052 | 250 | 500 | 486.8 | 0.404 | 5.32E-05 |
| 0.026 | 250 | 500 | 450.7 | 0.374 | 4.01E-04 |

TABLE 8-continued

| Wt. Ads. (g) | Vol. PO | PPB, Start | PPB, Final | C (mg/l) | q (g PPO/g Ads.) |
| --- | --- | --- | --- | --- | --- |
| 0.014 | 250 | 500 | 504.5 | 0.419 | −6.58E-05 |

Plots of the equilibrium concentration C of PPO against the amount of PPO adsorbed per unit weight of a particular diatomaceous earth in Examples 8–15 above show the ODW-C material to be most active, followed up the Dicalite 104 ™ material, the Filter-Cel ™ material and finally the Standard Super-Cel ™ material, which essentially showed no activity at all for PPO adsorption.

It is evident in any event from the foregoing examples that the process of the present invention, whether in a column-based treatment embodiment or in a slurry-based treatment embodiment, is well-adapted to produce a propylene oxide product which is suitable for the manufacture of acceptable polyether polyols for high resilient flexible polyurethane foam manufacture.

And while various embodiments of the present invention have been described and/or exemplified herein, those skilled in the art will recognize that numerous changes may be made in these embodiments without, however, departing in scope or spirit from the present invention as more particularly defined in the claims below.

What is claimed is:

1. A process for purifying propylene oxide containing an unacceptable quantity of poly(propylene oxide) contaminant having a molecular weight of at least about 50,000, comprising contacting the so-contaminated propylene oxide with a quantity of a substantially non-calcined diatomaceous earth for a time and under conditions sufficient to reduce the amount of such contaminant in such propylene oxide to acceptable levels, and recovering the purified propylene oxide product.

2. A process as defined in claim 1, wherein the diatomaceous earth has not been pyrolyzed to any appreciable extent.

3. A process as defined in claim 2, wherein the diatomaceous earth has a BET surface area of at least about 15 square meters per gram.

4. A process as defined in claim 3, wherein the diatomaceous earth has a BET surface area of at least about 35 square meters per gram.

5. A process as defined in claim 4, wherein the diatomaceous earth has a BET surface area of at least about 60 square meters per gram.

6. A process as defined in claim 5, wherein the diatomaceous earth shows at least about a 15 percent difference in its adsorption and desorption surface areas.

7. A process as defined in claim 6, wherein the diatomaceous earth shows at least about a 40 percent difference in its adsorption and desorption surface areas.

8. A process as defined in claim 7, wherein the diatomaceous earth shows at least about an 80 percent difference in its adsorption and desorption surface areas.

9. A process as defined in claim 6, wherein the diatomaceous earth has an average pore radius of about 120 Angstroms or less.

10. A process as defined in claim 1, wherein the purified propylene oxide product contains less than about 100 parts per billion (ppb) of said poly(propylene oxide) contaminant.

11. A process as defined in claim 10, wherein the purified propylene oxide product contains less than about 65 ppb of said poly(propylene oxide) contaminant.

12. A process as defined in claim 11, wherein the purified propylene oxide product contains less than about 50 ppb of said poly(propylene oxide) contaminant.

13. A process as defined in claim 1, wherein contacting the contaminated propylene oxide with the substantially non-calcined diatomaceous earth comprises slurrying the diatomaceous earth and contaminated propylene oxide together.

14. A process as defined in claim 1, wherein contacting the contaminated propylene oxide with the substantially non-calcined diatomaceous earth comprises passing the contaminated propylene oxide through a bed of the diatomaceous earth.

* * * * *